(12) United States Patent
Choi et al.

(10) Patent No.: US 11,559,064 B2
(45) Date of Patent: Jan. 24, 2023

(54) LACTOBACILLUS CURVATUS WIKIM55 HAVING ACTIVITY OF PROMOTING HAIR GROWTH, AND COMPOSITION CONTAINING SAME

(71) Applicant: KOREA FOOD RESEARCH INSTITUTE, Jeollabuk-do (KR)

(72) Inventors: Hak Jong Choi, Gwangju (KR); Min Sung Kwon, Gwangju (KR); Seul Ki Lim, Gwangju (KR); Young Joon Oh, Gwangju (KR); Ja Young Jang, Gwangju (KR); Ji Eun Lee, Busan (KR)

(73) Assignee: KOREA FOOD RESEARCH INSTITUTE, Jeollabuk-Do (KR)

( * ) Notice: Subject to any disclaimer, the term of this patent is extended or adjusted under 35 U.S.C. 154(b) by 243 days.

(21) Appl. No.: 16/617,613

(22) PCT Filed: May 30, 2018

(86) PCT No.: PCT/KR2018/006148
§ 371 (c)(1),
(2) Date: Nov. 27, 2019

(87) PCT Pub. No.: WO2018/221956
PCT Pub. Date: Dec. 6, 2018

(65) Prior Publication Data
US 2020/0178565 A1    Jun. 11, 2020

(30) Foreign Application Priority Data

Jun. 1, 2017 (KR) .................. 10-2017-0068238

(51) Int. Cl.
*A23K 10/16* (2016.01)
*A23L 29/00* (2016.01)
*A23L 33/135* (2016.01)
*A61K 35/747* (2015.01)

(52) U.S. Cl.
CPC ............ *A23K 10/16* (2016.05); *A23L 29/065* (2016.08); *A23L 33/135* (2016.08); *A61K 35/747* (2013.01)

(58) Field of Classification Search
CPC ........ A23K 10/16; A23K 10/18; A23L 29/065
USPC .......................................................... 426/61
See application file for complete search history.

(56) References Cited

U.S. PATENT DOCUMENTS

2015/0306158 A1    10/2015 Kim

FOREIGN PATENT DOCUMENTS

| EP | 1097700 | 5/2001 |
|---|---|---|
| JP | 2004-210659 | 7/2004 |
| JP | 2015-187171 | 10/2015 |
| KR | 1020140032413 | 3/2014 |
| KR | 1020140032427 | 3/2014 |
| KR | 1020140143121 | 12/2014 |
| KR | 1020160070508 | 6/2016 |
| KR | 1020160096158 | 8/2016 |
| KR | 10-1680014 | 11/2016 |
| KR | 1018017640000 | 11/2017 |
| WO | 2000/69399 | 11/2000 |
| WO | 2010/013182 | 2/2010 |

OTHER PUBLICATIONS

KR 2014 143121—English Abstract (Year: 2014).*
JP-2010-143-885-English Abstract pp. 27-28 (Year: 2010).*
Jo, S., et al., "Lactobacillus curvatus WiKim38 isolated from kimchi induces IL-10 production in dendritic cells and alleviates DSS-induced colitis in mice," Journal of Microbiology (2016) vol. 54, No. 7, pp. 503-509.

* cited by examiner

*Primary Examiner* — Hamid R Badr
(74) *Attorney, Agent, or Firm* — Duane Morris LLP; Gregory M. Lefkowitz; Brandon A. Chan

(57) ABSTRACT

The present disclosure relates to novel *Lactobacillus curvatus* WIKIM55 isolated from kimchi, and a composition containing the same. The *Lactobacillus curvatus* WIKIM55 according to the present disclosure is a probiotic having activities of promoting hair growth and can be diversely applied for intestinal regulation and promotion of hair growth in humans or animals.

2 Claims, 3 Drawing Sheets
Specification includes a Sequence Listing.

LACTOBACILLUS CURVATUS WIKIM55 HAVING ACTIVITY OF PROMOTING HAIR GROWTH, AND COMPOSITION CONTAINING SAME

CROSS-REFERENCE TO RELATED APPLICATIONS

This application is a § 371 national stage entry of International Application No. PCT/KR2018/006148, filed on May 30, 2018, which claims priority to Korean Patent Application No. 10-2017-0068238, filed Jun. 1, 2017, the entire contents of which are incorporated herein by reference.

TECHNICAL FIELD

The present disclosure relates to a novel *Lactobacillus curvatus* strain and a composition containing the same.

BACKGROUND ART

Hair is a body organ which plays the roles of protecting the head, maintain the head temperature, etc. and determines appearance, which draws a lot of interests recently. Accordingly, the interest in hair loss and hair loss treatment is increasing, and research and development on hair loss treatments are being carried out actively. Hair grows and sheds through the hair cycle of 4 stages: anagen (growth phase), catagen (transitional phase), telogen (resting phase) and exogen (shedding phase). Hair loss refers to a loss of hair caused when hair shedding excels hair growth for various reasons. The currently known causes of hair loss include genetic factors, problems with blood flow, endocrine disorders caused by the male hormone testosterone, etc. Also, stress is known as an external cause.

As typical hair growth promoting agents, minoxidil (6-amino-1,2-dihydro-1-hydroxy-2-imino-4-phenoxypyrimidine, percutaneous liniment), finasteride (oral agent), etc. are used. Minoxidil is known to induce hair growth by promoting supply of nutrients through vasodilation. Finasteride has a mechanism of action of inhibiting the death of dermal papilla cells through inhibition of the activity of 5α-reductase, which is an enzyme involved in testosterone metabolism. However, both drugs are effective only during their use and the effect disappears if the use is stopped. Therefore, they have to be used for a long period of time. But, because minoxidil has the side effect of sticky feeling and skin irritation and finasteride has the side effects of decline in energy, sexual dysfunction, etc., there are many limitations in their long-term use.

Under this background, studies on skin and hair health using lactic acid bacteria are underway, recently. But, the lactic acid bacteria that directly affect hair growth have not been found yet and the development of a composition containing excellent lactic acid bacteria capable of leading to hair health and hair growth is required.

DISCLOSURE

Technical Problem

The present disclosure is directed to providing novel lactic acid bacteria in the genus *Lactobacillus* having superior activity of promoting hair growth.

Technical Solution

The inventors of the present disclosure have made efforts to a lactic acid bacteria strain showing an effect of promoting hair growth while exhibiting excellent effect as a probiotic from traditional fermented foods. As a result, they have isolated and identified the novel lactic acid bacteria strain of the genus *Lactobacillus*, *Lactobacillus curvatus* WIKIM55, and have completed the present disclosure.

Thus, the present disclosure provides a pharmaceutical composition and a food composition for promoting hair growth, which contain *Lactobacillus curvatus* WIKIM55 or a culture thereof as an active ingredient, a method for promoting hair growth, which includes administering a therapeutically effective amount of *Lactobacillus curvatus* WIKIM55 or a culture thereof to a subject in need thereof, and a novel use of *Lactobacillus curvatus* WIKIM55 for promoting hair growth.

The *Lactobacillus curvatus* WIKIM55 according to the present disclosure is a novel strain of *Lactobacillus curvatus* originating from kimchi. Although the *Lactobacillus curvatus* WIKIM55 according to the present disclosure is isolated from kimchi, its origin is not limited thereto.

In an example of the present disclosure, the lactic acid bacteria strain showing an excellent effect as a probiotic, which was isolated from traditional fermented food, was found to have a nucleic acid sequence of SEQ ID NO: 1 when subjected to 16S rDNA sequence analysis for the identification and classification of microorganisms.

The microorganism having the 16S rDNA base sequence of SEQ ID NO: 1 was named *Lactobacillus curvatus* WIKIM55 and deposited on Apr. 7, 2017 in the Korean Culture Center of Microorganisms (accession number: KCCM12011P).

The *Lactobacillus curvatus* WIKIM55 of the present disclosure is a Gram-positive bacterium. It is a rod-shaped facultative anaerobe capable of growing under both aerobic and anaerobic conditions without forming spores.

The *Lactobacillus curvatus* WIKIM55 of the present disclosure is a probiotic and has the intestinal regulation and immunity enhancement effects of general lactic acid bacteria. It is well known that the lactic acid bacteria in the genus *Lactobacillus* have the effect of relieving intestinal disorders and enhancing immunity.

In the present disclosure, the 'probiotic' is understood to mean live microorganisms that provide health benefits to a host improving the host's intestinal microbial environment in the gastrointestinal tract of animals including human. The probiotics are live microorganisms having probiotic activity and can have a beneficial effect on the host's intestinal flora when provided to human or animals in the form of single or multiple strains.

In the following examples, it was confirmed that the strain *Lactobacillus curvatus* WIKIM55 of the present disclosure exhibits an effect of promoting hair growth by promoting hair follicle formation. Therefore, the *Lactobacillus curvatus* WIKIM55 according to the present disclosure may be utilized for various uses, such as intestinal regulation, promotion of hair growth, enhancement of immunity, etc. in human or animals.

In the present disclosure, the effect of "promoting hair growth" means promoting the growth of hair and ultimately increasing the proportion hair in the anagen from the entire hair. Thus, the term means the inhibition of hair loss caused by decreased proportion of hair in the anagen and may have the same meaning as "hair loss improvement", "hair loss prevention" and "hair loss treatment".

Thus, an exemplary embodiment of the present disclosure provides a probiotic composition containing *Lactobacillus curvatus* WIKIM55 or a culture thereof.

The *Lactobacillus curvatus* WIKIM55 contained in the composition according to the present disclosure may exist as live cells or dead cells, and also may exist in dried or lyophilized form. The forms of lactic acid bacteria suitable for inclusion in a variety of compositions and formulation method thereof are well known to those skilled in the art.

In one exemplary embodiment, the composition may be a composition for oral administration which contains the *Lactobacillus curvatus* WIKIM55 strain present as live cells.

In another exemplary embodiment, the composition can be a composition for external for application to skin, which contains a culture or a lysate of the *Lactobacillus curvatus* WIKIM55 strain or a fermented product using the strain.

In one exemplary embodiment, the present disclosure provides an intestinal regulation composition containing *Lactobacillus curvatus* WIKIM55 or a culture thereof. The intestinal regulation composition according to the present disclosure may be used for prevention, treatment and improvement of gastrointestinal diseases of animals including human. Specifically, the animals include farm animals such as cow, horse and pig. The "gastrointestinal disease" includes infection by bacteria affecting the stomach and inflammatory bowel diseases. For example, infectious diarrhea caused by pathogenic bacteria (*E. coli, Salmonella, Clostridium*, etc.), gastrointestinal inflammation, inflammatory bowel disease, neurogenic enteritis syndrome, small intestine bacterial overgrowth syndrome, intestinal dysentery diarrhea, etc. are included, although not being limited thereto.

Specifically, the intestinal regulation composition according to the present disclosure may be administered orally. The administration dose can vary depending on the type of gastrointestinal disease, severity of disease, age, sex, ethnicity, therapy or prophylaxis. In general, one thousand to hundred billion bacteria may administered a day, for adults.

The present disclosure provides a composition for enhancing immunity, which contains *Lactobacillus curvatus* WIKIM55 or a culture thereof. It is well known that lactic acid bacteria in the genus *Lactobacillus* have the effect of intestinal regulation and enhancement of immunity.

The present disclosure provides a composition for promoting hair growth, which contains *Lactobacillus curvatus* WIKIM55 or a culture thereof.

The *Lactobacillus curvatus* WIKIM55 according to the present disclosure may be contained in pharmaceuticals, health foods, foods, feeds, feed additives, lactic acid starters or cosmetics due to these beneficial effects.

In one exemplary embodiment, the present disclosure provides a pharmaceutical composition for promoting hair growth, which contains *Lactobacillus curvatus* WIKIM55 or a culture thereof as an active ingredient.

When the composition of the present disclosure is used as a pharmaceutical composition, the pharmaceutical composition of the present disclosure may be prepared using an adjuvant that is pharmaceutically suitable and physiologically acceptable in addition to the active ingredient. As the adjuvant, an excipient, a disintegrant, a sweetening agent, a binder, a coating agent, a swelling agent, a lubricant, a glidant, a flavoring agent, etc. may be used.

Specifically, the pharmaceutical composition may be formulated by adding one or more pharmaceutically acceptable carrier in addition to the active ingredient described above for administration of the pharmaceutical composition.

The formulation form of the pharmaceutical composition may be a granule, a powder, a tablet, a coated tablet, a capsule, a suppository, a solution, a syrup, a juice, a suspension, an emulsion, a drop, an injectable solution, etc. For example, for formulation into the form of a tablet or a capsule, the active ingredient may be combined with an oral, non-toxic, pharmaceutically acceptable inert carrier such as ethanol, glycerol, water etc. Moreover, if desired or needed, a suitable binder, lubricant, disintegrant and coloring agent may also be included in the mixture. A suitable binder includes, but is not limited to, starch, gelatin, a natural sugar such as glucose or beta-lactose, a corn sweetener, a natural or synthetic gum such as acacia, tragacanth or sodium oleate, sodium stearate, magnesium stearate, sodium benzoate, sodium acetate, sodium chloride, and the like. The disintegrant includes, but is not limited to, starch, methyl cellulose, agar, bentonite, xanthan gum, and the like.

As in an acceptable pharmaceutical carrier in a composition formulated into a liquid solution, one or more ingredient of saline, sterile water, Ringer's solution, buffered saline, albumin injection solution, dextrose solution, maltodextrin solution, glycerol and ethanol, which are sterilized and suitable for the living body, may be mixed. Other conventional additives such as an antioxidant, a buffer, a bacteriostatic agent, etc. may be added, if necessary. In addition, a diluent, a dispersant, a surfactant, a binder or a lubricant may be added additionally for formulation into an injectable formulation such as an aqueous solution, a suspension, an emulsion, etc., a pill, a capsule, a granule or a tablet.

Moreover, the formulation may be performed according to the corresponding diseases or ingredients using the methods disclosed in Remington's Pharmaceutical Science, Mack Publishing Company, Easton Pa.

In addition, the present disclosure provides a method for promoting hair growth, which includes administering a therapeutically effective amount of *Lactobacillus curvatus* WIKIM55 or a culture thereof to a subject in need thereof.

The term "subject" used herein refers to a mammal that is the subject of treatment, observation or experiment. Specifically, it refers to human.

Further, the term "therapeutically effective amount" as used herein means the amount of an active ingredient or a pharmaceutical composition for inducing a biological or medical response in the tissue system, animal or human determined by a researcher, a veterinarian, a doctor or a clinician. It includes the amount of inducing relief of symptoms of the disease or disorder being treated. It is obvious to those skilled in the art that the therapeutically effective amount and number of administrations of the active ingredient of the present disclosure will be changed depending on the desired effect. Therefore, the optimum dosage to be administered may be readily determined by those of skilled in the art, and can be adjusted depending on a variety of factors including the type of a disease, the severity of the disease, the contents of the active ingredient and other ingredients contained in the composition, the type of formulation, the age, body weight, general health condition, sex and diet of a patient, administration time, administration route, the excretion rate of the composition, treatment period and a drug used together. Specifically, in the treatment method of the present disclosure, the *Lactobacillus curvatus* WIKIM55 or a culture thereof may be administered with a dose of 0.01 mg/kg to 200 mg/kg for an adult, once or several times a day.

In the treatment method of the present disclosure, the composition of the present disclosure containing *Lactobacillus curvatus* WIKIM55 or a culture thereof as an active ingredient may be administered according to a common method via oral, rectal, intravenous, intraarterial, intraperitoneal, intramuscular, intrasternal, transdermal, topical, intraocular or intradermal route.

In another exemplary embodiment, the present disclosure provides a food composition for promoting hair growth, which contains *Lactobacillus curvatus* WIKIM55 or a culture thereof as an active ingredient. The food composition may be in the form of a functional food, a beverage, a bar, etc.

In the present disclosure, the food composition containing the strain as an active ingredient may include a beverage such as fermented milk, etc. Thus, the present disclosure provides a lactic acid bacteria starter for fermentation, which contains *Lactobacillus curvatus* WIKIM55 or a culture thereof.

The food composition according to the present disclosure may be formulated in the same way as the pharmaceutical composition and can be used as a functional food or added to various foods. The foods to which the composition of the present disclosure can be added include, for example, a beverage, an alcoholic beverage, confectionery, a diet bar, a dairy product, meat, chocolate, pizza, an instant noodle, a gum, ice cream, a vitamin complex, a health supplement, and so on.

For example, if the food composition of the present disclosure is prepared as a beverage such as a drink, it may further contain citric acid, fructose syrup, sugar, glucose, acetic acid, malic acid, fruit juice, various plant extracts, etc. in addition to *Lactobacillus curvatus* WIKIM55 or a culture thereof.

In addition, the present disclosure may provide a functional food containing the *Lactobacillus curvatus* WIKIM55 or a culture thereof. The functional food refers to a food prepared by adding *Lactobacillus curvatus* WIKIM55 or a culture thereof to a food material such as a drink, a tea, a gum, confectionery, etc. or prepared by encapsulation, pulverization, suspension, etc., which, if ingested, brings specific health benefits, but, unlike generic drugs, has the advantage of no side effect that can occur during long-term use. Thus, the functional food of the present disclosure obtained as such is very useful because it is can be ingested routinely. The addition amount of *Lactobacillus curvatus* WIKIM55 or a culture thereof in such health food cannot be uniformly defined because it can vary depending on the type of the health food. The amount may be in a range which does not impair the original taste of the food and may be 0.01 to 50% by weight, specifically 0.1 to 20% by weight, with respect to the food to which it is added. In the case of a food in the form of a granule, a tablet or a capsule, it may be added in a range of usually 0.1 to 100% by weight, specifically 0.5 to 80% by weight. In one exemplary embodiment, the functional food of the present disclosure may be in the form of a drink.

The composition according to the present disclosure may be used as a feed additive or a feed.

When used as a feed additive, the composition may be prepared into a solution with a high concentration of 20 to 90%, or a powder or granule. The feed additive may further contain one or more of an organic acid such as citric acid, fumaric acid, adipic acid, lactic acid, malic acid, etc. a phosphate such as sodium phosphate, potassium phosphate, acidic pyrophosphate, polyphosphate, etc., or a natural antioxidant such as polyphenol, catechin, alpha-tocopherol, rosemary extract, vitamin C, green tea extract, licorice root extract, chitosan, tannic acid, phytic acid, etc. When used as a feed, the composition may be formulated into an ordinary feed and may further contain common feed ingredients.

The feed additive and feed may further contain, a cereal, e.g., ground or crushed wheat, oats, barley, maize and rice; a vegetable protein feed, e.g., a feed containing rape, soya and sunflower as main ingredients; an animal protein feed, e.g., blood meal, metal meal, bone meal and fish meal; a sugar or milk, e.g., a dry ingredient composed of a variety of powder milk and whey powder. In addition, a nutritional supplement, a digestion- and absorption-enhancing agent, a growth-promoting agent, etc. may be further contained.

The feed additive may be administered to an animal either alone or in combination with other feed additives in an edible carrier. Further, the feed additive may be mixed directly into an animal feed as a top dressing or may be administered easily to an animal as an oral dosage form separately from a feed. When the feed additive is administered separately from an animal feed, it can be prepared into an immediate-release or sustained-release formulation in combination with a pharmaceutically acceptable edible carrier as is well known in the art. The edible carrier may be either solid or liquid, such as corn starch, lactose, sucrose, soy flakes, peanut oil, olive oil, sesame oil and propylene glycol. If a solid carrier is used, the feed additive may be in the form of a tablet, a capsule, a powder, a troche, a sugar-coated tablet or a top dressing. If a liquid carrier is used, the feed additive may be in the form of a soft gelatin capsule, a syrup, a suspension, an emulsion or a solution.

Further, the feed additive and the feed can contain an adjuvant, for example, a preservative, a stabilizer, a wetting or emulsifying agent, a solubilizing promoter, etc. The feed additive may be added to an animal feed through spraying or mixing.

The feed or feed additive of the present disclosure can be provided to a large number of animals, including mammals, poultry and fish.

The mammal may include pig, cow, sheep, goat, laboratory rodents and pets (e.g., dog and cat). The poultry may include chicken, turkey, duck, goose, pheasant, quail, etc., and the fish may include trout, etc., although not being limited thereto.

In one exemplary embodiment, the feed or feed additive can be used for promotion of hair growth of pets. The pet includes, dog, cat, rat, rabbit, etc., although not being limited thereto.

Further, when the composition is used as a cosmetic composition, the cosmetic composition may be formulated into an external composition for skin or a scalp cleanser, although not being particularly limited thereto. The external composition for skin may be, for example, a softening lotion, a nourishing lotion, a massage cream, a nourishing cream, a pack, or a gel, and may be a formulation for transdermal administration such as a lotion, an ointment, a gel, a cream, a patch or a spray. The scalp cleanser may be formulated, for example, as a hair spray, a hair tonic, a hair conditioner, a hair essence, a hair lotion, a hair nourishing lotion, a hair shampoo, a hair rinse, a hair treatment, a hair cream, a hair nourishing cream, a hair moisturizing cream, a hair massage cream, a hair wax, a hair aerosol, a hair pack, a hair nourishing pack, a hair soap, a hair cleansing foam, a hair dye, a hair waving agent, a hair bleach, a hair gel, a hair glaze or a hair mousse, although not being limited thereto. In the external composition of the respective formulations, ingredients other than the strain *Lactobacillus curvatus* WIKIM55 strain selected by those skilled in the art without difficulty may be added depending on the formulation or use of the external composition.

Specifically, the cosmetic composition of the present disclosure contains a cosmetically acceptable medium or base. It may be provided as all possible formulations suitable for topical application, for example, a solution, a gel, a solid or anhydrous paste, an emulsion obtained by dispersing an oil phase in a water phase, a suspension, a microemulsion, microcapsule, a microgranule, an ionic (liposome) and/or non-ionic vesicular dispersion, a cream, a skin lotion, a powder, an ointment, a spray or a conceal stick. Further, it may also be prepared into a foam or an aerosol composition further containing a compressed propellant. In addition, the cosmetic composition of the present disclosure can be prepared into an adjuvant that can be applied topically or systematically, which is commonly used in the dermatological field, by including a dermatologically acceptable medium or base, and these compositions can be prepared according to the methods common in the art.

In addition, the present disclosure of the cosmetic composition may contain an adjuvant commonly used in the dermatological field, such as a fatty substance, an organic solvent, a solubilizing agent, a thickener, a gelling agent, a softener, an antioxidant, a suspending agent, a stabilizer, a foaming agent, an odorant, a surfactant, water, an ionic or non-ionic emulsifying agent, a filler, a metal ion sequestering agent, a chelating agent, a preservative, a vitamin, a blocker, a moisturizing agent, an essential oil, a dye, a pigment, a hydrophilic or lipophilic activator, a lipid vesicle or any other ingredient commonly used in cosmetics. These adjuvants are incorporated in amounts commonly used in the cosmetic field.

The amount of the *Lactobacillus curvatus* WIKIM55 strain contained in the composition according to the present disclosure may be from about $10^6$ to $10^{12}$ CFU/g, e.g., $10^7$ to $10^{11}$ CFU/g or $10^8$ to $10^{10}$ CFU/g, based on a single dose. Specifically, the strain may be administered as live bacteria, and may be killed or attenuated before intake. Further, a sterilization process through heat treatment may be performed additionally when the composition is prepared by using a culture supernatant, etc. The amount of the strain required to achieve a minimal effect and the daily dose thereof may vary depending on the physical or health condition of a patient. Generally, the daily dose can be about $10^6$ to $10^{12}$ CFU/g, e.g., $10^7$ to $10^{11}$ CFU/g or $10^8$ to $10^{10}$ CFU/g.

The advantages and features and the methods of accomplishing the same will become apparent by the following examples described in detail. However, the present disclosure is not limited to the examples set forth below but may be embodied in many different forms. The examples are provided such that the disclosure of the present disclosure is complete and are provided to fully inform the scope of the invention to those having ordinary knowledge in the art to which the present disclosure belongs. The scope of the present disclosure will only be defined by the appended claims.

Advantageous Effects

Because *Lactobacillus curvatus* WIKIM55 according to the present disclosure exhibits an activity of promoting hair growth, it can be utilized variously as a probiotic for uses such as intestinal regulation, enhancement of immunity, promotion of hair growth, etc. in human or animals. Furthermore, it can be usefully used as a starter for fermentation.

Deposits

The Deposit with Korean Culture Center of Microorganisms, under deposit accession number KCCM12011P was made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

Best Mode

Figure 1:
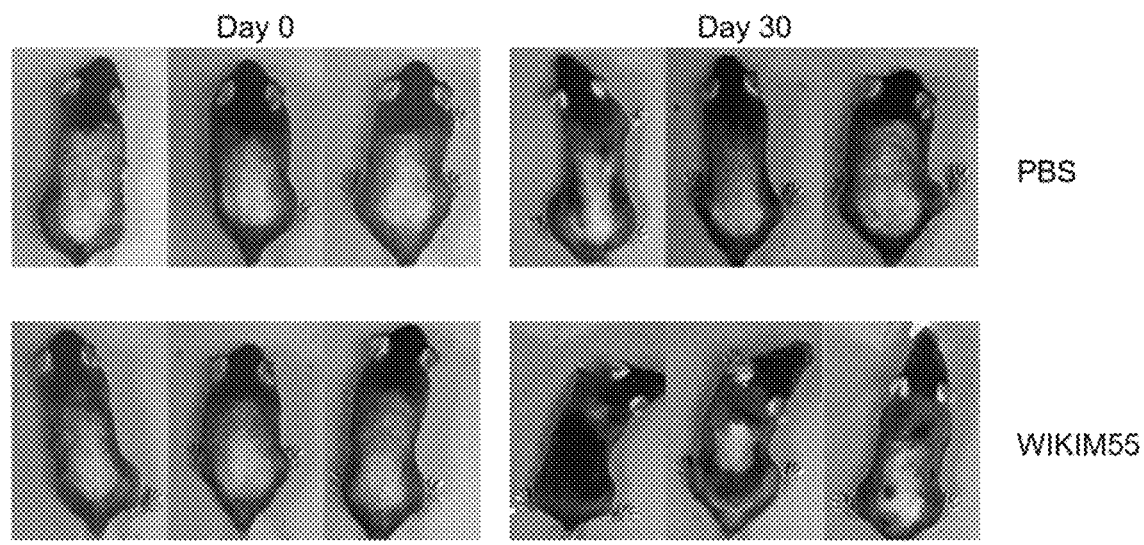
FIG. 1 shows a result of observing the hair growth pattern of mice fed with the strain of the present disclosure for 30 days with the naked eye.

Hereinafter, the present disclosure will be described in detail through examples. However, the following examples are for illustrative purposes only and the scope of the present disclosure is not limited by the examples.

EXAMPLES

Example 1: Isolation and Identification of Strain

A bacterial single colony obtained by smearing a crude liquid extract of kimchi in MRS culture medium was collected and cultured in MRS broth. DNA was extracted using the QIAamp DNA Mini Kit (QIAgen, Germany). The extracted DNA was confirmed using 1% agarose gel. PCR was conducted using the extracted genomic DNA as a template to amplify the 16S rDNA gene. The PCR condition was 30 cycles of denaturation at 95° C. for 1 minute, annealing at 45° C. for 1 minute and extension at 72° C. for 1 minute and 30 seconds. The sequence of the PCR product obtained was analyzed by Macrogen (Seoul, Korea). Bacterial identification was performed via similarity analysis of the Basic Local Alignment Search Tool (BLAST) search engine of the National Center for Biotechnology Information (NCBI, www.ncbi.nlm.nih.gov) of the 16S rDNA sequence.

As a result of the 16S rDNA base sequence analysis for identification of microorganisms, the strain isolated in this example was found to have a nucleic acid sequence of SEQ ID NO: 1.

The microorganism of the present disclosure was named *Lactobacillus curvatus* WIKIM55 and deposited on Apr. 7, 2017 in the Korea Culture Center of Microorganisms (accession number: KCCM12011P).

16S rDNA sequence of *Lactobacillus curvatus* WIKIM55
SEQ ID NO: 1

ACATGCAAGTCGAACGCACTCTCGTTAGATTGAAGAAGCTTGCTTCTGAT
TGATAACATTTGAGTGAGTGGCGGACGGGTGAGTAACACGTGGGTAACCT
GCCCTAAAGTGGGGGATAACATTTGGAAACAGATGCTAATACCGCATAAA
ACCTAGCACCGCATGGTGCAAGGTTGAAAGATGGTTTCGGCTATCACTTT
AGGATGGACCCGCGGTGCATTAGTTAGTTGGTGAGGTAAAGGCTCACCAA
GACCGTGATGCATAGCCGACCTGAGAGGGTAATCGGCCACACTGGGACTG
AGACACGGCCCAGACTCCTACGGGAGGCAGCAGTAGGGAATCTTCCACAA
TGGACGAAAGTCTGATGGAGCAACGCCGCGTGAGTGAAGAAGGTTTTCGG
ATCGTAAAACTCTGTTGTTGGAGAAGAACGTATTTGATAGTAACTGATCA
GGTAGTGACGGTATCCAACCAGAAAGCCACGGCTAACTACGTGCCAGCAG
CCGCGGTAATACGTAGGTGGCAAGCGTTGTCCGGATTTATTGGGCGTAAA
GCGAGCGCAGGCGGTTTCTTAAGTCTGATGTGAAAGCCTTCGGCTCAACC
GAAGAAGTGCATCGGAAACTGGGAAACTTGAGTGCAGAAGAGGACAGTGG
AACTCCATGTGTAGCGGTGAAATGCGTAGATATATGGAAGAACACCAGTG
GCGAAGGCGGCTGTCTGGTCTGTAACTGACGCTGAGGCTCGAAAGCATGG
GTAGCAAACAGGATTAGATACCCTGGTAGTCCATGCCGTAAACGATGAGT
GCTAGGTGTTGGAGGGTTTCCGCCCTTCAGTGCCGCAGCTAACGCATTAA
GCACTCCGCCTGGGGAGTACGACCGCAAGGTTGAAACTCAAAGGAATTGA
CGGGGGCCCGCACAAGCGGTGGAGCATGTGGTTTAATTCGAAGCAACGCG
AAGAACCTTACCAGGTCTTGACATCCTTTGACCACTCTAGAGATAGAGCT
TTCCCTTCGGGGACAAAGTGACAGGTGGTGCATGGTTGTCGTCAGCTCGT
GTCGTGAGATGTTGGGTTAAGTCCCGCAACGAGCGCAACCCTTATTACTA
GTTGCCAGCATTTAGTTGGGCACTCTAGTGAGACTGCCGGTGACAAACCG
GAGGAAGGTGGGGACGACGTCAAATCATCATGCCCCTTATGACCTGGGCT
ACACACGTGCTACAATGGATGGTACAACGAGTCGCGAGACCGCGAGGTTT
AGCTAATCTCTTAAAACCATTCTCAGTTCGGATTGTAGGCTGCAACTCGC
CTACATGAAGCCGGAATCGCTAGTAATCGCGGATCAGCATGCCGCGGTGA
ATACGTTCCCGGGCCTTGTACACACCGCCCGTCACACCATGAAGAGTTTG
TAACACCCAAAGCCGGGTGAGGTAACCTTCGGGAGCCAGCCGTCTAAGG.

Example 2: Confirmation of Hair Growth Promoting Effect of *Lactobacillus curvatus* WIKIM55

The *Lactobacillus curvatus* WIKIM55 strain isolated in Example 1 was cultured in MRS medium at 30° C. for 24 hours, and the cultured bacteria were centrifuged at 8,000 rpm for 5 minutes and then washed with PBS to remove the remaining medium components. Then, the number of the bacteria was quantified to be $1 \times 10^{19}$ CFU/mL using PBS, and 0.2 mL ($2 \times 10^9$ CFU) was orally administered to test animals, five times a week, using a sonde. Sterile PBS was administered to negative and positive control groups.

1) Sensory Evaluation 6-week-old mice (C57/BL6) ahead of the telogen phase were accustomed in the breeding room for one week and the hair on the back was removed using a hair removing apparatus for animals. Then, after orally administrating *Lactobacillus curvatus* WIKIM55 for 30 days, the hair growth pattern was evaluated by clinical visual evaluation.

As a result, the group fed with the *Lactobacillus curvatus* WIKIM55 strain (WIKIM55) showed faster hair growth as compared with the control group fed with PBS (PBS), as shown in FIG. 1.

2) Measurement of Skin Thickness

Figure 2:
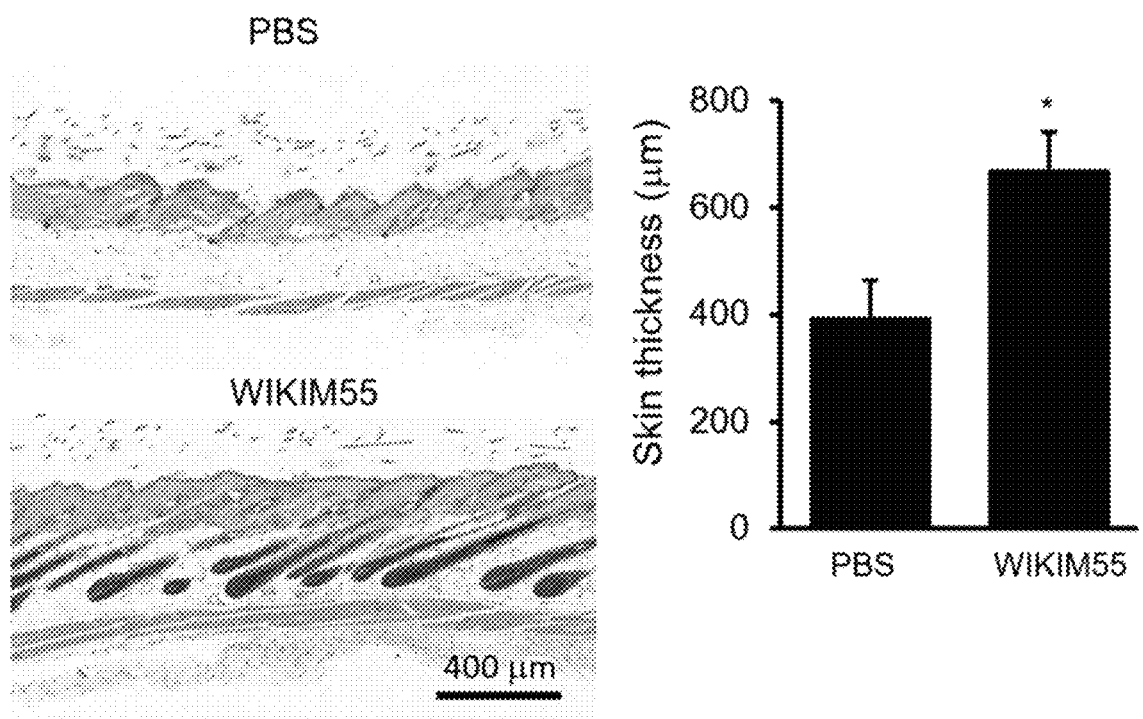
FIG. 2 shows the skin tissue of a mouse fed with the strain of the present disclosure and a result measuring the skin thickness.

Hair repeats growth and shedding through the hair cycle. It is known that, during the anagen phase when hair grows, the skin layer becomes thicker and hair follicles exist primarily in the subcutaneous layer of the skin. Thus, the skin tissue and skin thickness were investigated 30 days after the hair of the mice was removed (FIG. 2).

As a result, the skin thickness of the PBS-treated group was 393.28 μm, whereas the group fed with *Lactobacillus curvatus* WIKIM55 had a skin thickness of 670.95 μm. It was also confirmed that most of the hair follicles were present in the subcutaneous layer. Through this, it confirmed that most of the hair follicles of the group fed with *Lactobacillus curvatus* WIKIM55 were in the anagen phase.

3) Measurement of Number of Hair Follicles in Subcutaneous Tissue

The number of hair follicles in the subcutaneous tissue was measured 30 days after the hair of the mice was removed.

Figure 3:
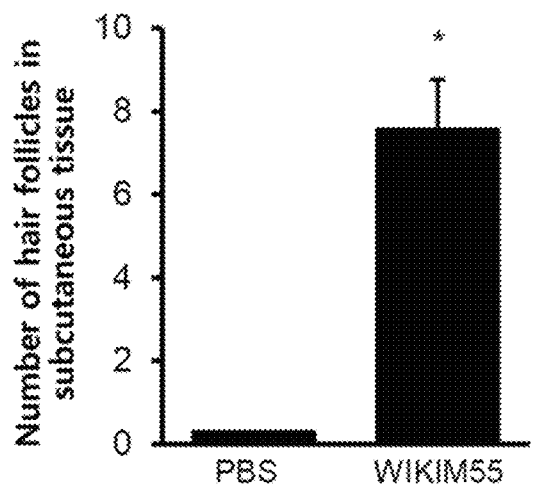
FIG. 3 shows a result of measuring the number of hair follicles in the subcutaneous tissue of a mouse fed with the strain of the present disclosure.

As a result, the number of hair follicles was significantly larger for the group fed with *Lactobacillus curvatus* WIKIM55 than the PBS-treated group, as shown in FIG. 3

Example 3: Confirmation of Hair Growth Promoting Effect of *Lactobacillus curvatus* WIKIM55

The *Lactobacillus curvatus* WIKIM55 strain isolated in Example 1 was cultured in MRS medium at 30° C. for 24 hours, and the cultured bacteria were centrifuged at 8,000 rpm for 5 minutes and then washed with PBS to remove the remaining medium components. Then, the number of the bacteria was quantified to be $1 \times 10^{19}$ CFU/mL using PBS, and 0.2 mL ($2 \times 10^9$ CFU) was orally administered to test animals, five times a week, using a sonde. Sterile PBS was administered to negative and positive control groups.

1) Sensory Evaluation 6-week-old mice (C57/BL6) ahead of the telogen phase were accustomed in the breeding room for one week and the hair on the back was removed using a hair removing apparatus for animals. After orally administrating *Lactobacillus curvatus* WIKIM55 for 20 weeks, the hair growth pattern was evaluated by clinical visual evaluation.

Figure 4:
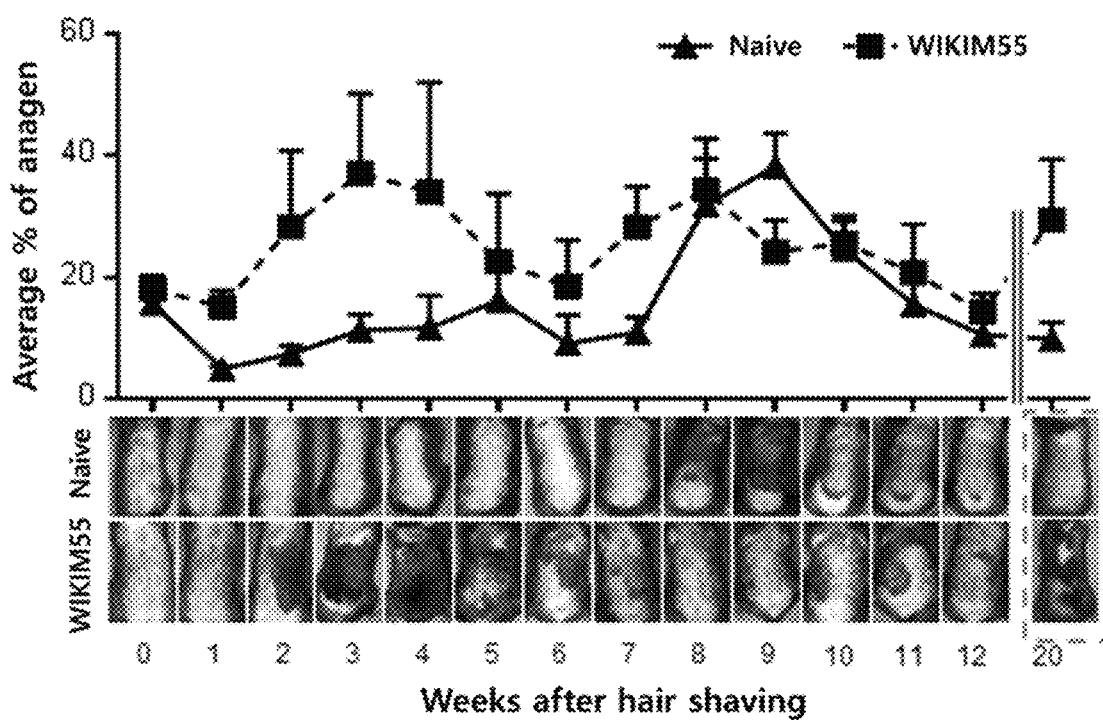
FIG. 4 shows a result of observing the hair growth pattern of a mouse fed with the strain of the present disclosure for 20 weeks and identifying the anagen.

As shown in FIG. 4, whereas the control group (PBS) fed with PBS had the anagen phase after about 7 weeks of the resting phase, the group fed with the *Lactobacillus curvatus* WIKIM55 strain (WIKIM55) switched to the anagen phase after about 2-3 weeks of the resting phase, leading to faster hair growth.

2) Confirmation of Distribution of Hair Follicle Stem Cells

In order to compare the distribution of hair follicle stem cells of the mice of the control group (PBS) and the group fed with *Lactobacillus curvatus* WIKIM55 for 20 weeks (WIKIM55), the skin tissue on the back was excised. After removing subcutaneous fat from the excised tissue and then washing with phosphate buffered saline (PBS), the tissue was placed in RPM11640 culture medium containing 4 mg/mL collagenase IV, 2 mg/mL hyaluronidase and 100 U/mL DNase I and hair follicle stem cells were isolated from the skin tissue using the gentleMACS dissociator (Miltenyibiotec, Germany). FACS (fluorescence-activated cell sorting) analysis was performed to investigate the distribution of the hair follicle stem cells. The verified antigens showed the immunological characteristics of CD45-CD34+ CD49f+. $1 \times 10^5$ cells isolated from the skin tissue were washed with PBS solution containing 2% FBS and were allowed to react at room temperature with antibodies for the respective antigens. The expression of the antigens was confirmed by flow cytometry.

Figure 5:
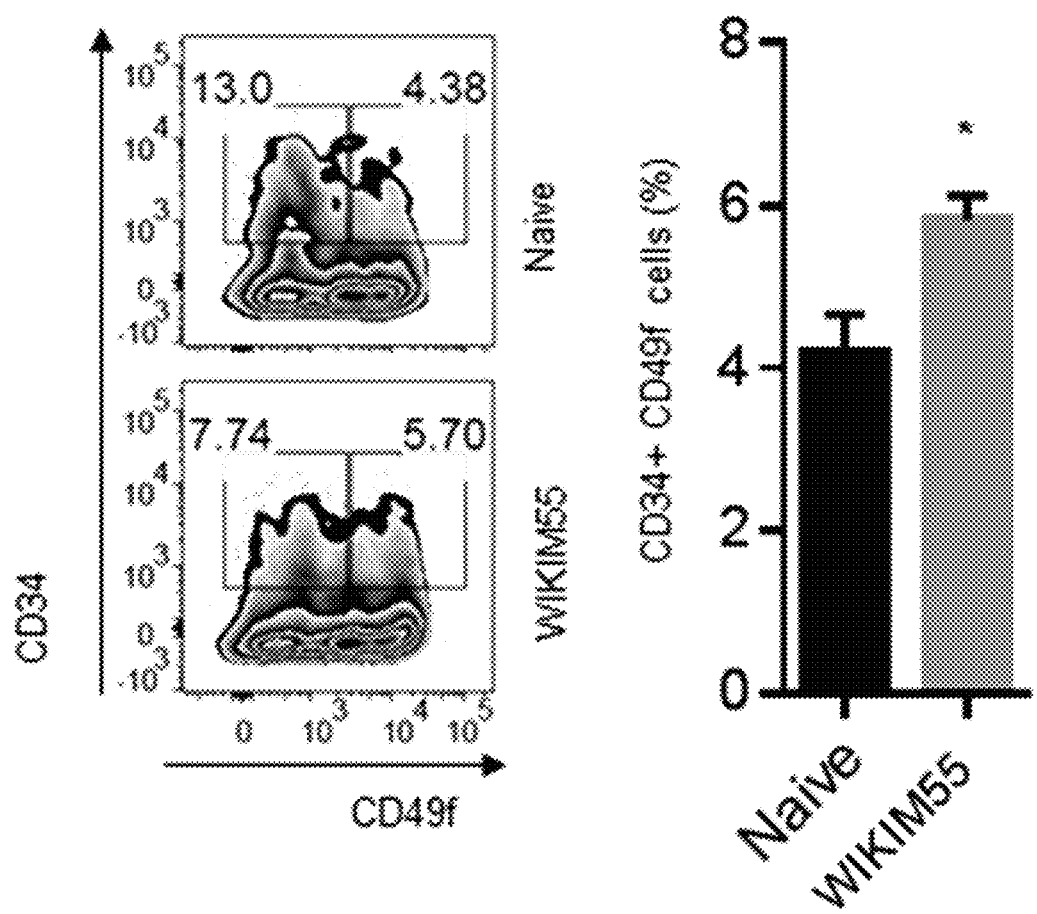
FIG. 5 shows a result of confirming the distribution of follicular stem cells of a mouse fed with the strain of the present disclosure by FACS analysis.

As can be seen from FIG. 5, it was confirmed that more hair follicle stem cells showing the immunological characteristics of CD34+ CD49f+ were distributed in the skin tissue of the in the group fed with WIKIM55 as compared to the control group (PBS, naive). Because the hair follicle stem cells are involved in the growth of new hair, it is thought that the intake of WIKIM55 will increase hair growth by producing hair follicle stem cells.

The invention claimed is:

1. A method for promoting hair growth, which comprises administering *Lactobacillus curvatus* WIKIM55 (accession number KCCM12011P) or a culture thereof to a subject, wherein *Lactobacillus curvatus* WIKIM55 (accession number KCCM12011P) is derived from kimchi and the *Lactobacillus curvatus* WIKIM55 (accession number KCCM12011P) or a culture thereof is administered orally.

2. The method according to claim 1, wherein the *Lactobacillus curvatus* WIKIM55 (accession number KCCM12011P) or a culture thereof promotes hair growth by increasing the number of hair follicles in the anagen phase.

* * * * *

```
                        SEQUENCE LISTING

<160> NUMBER OF SEQ ID NOS: 1

<210> SEQ ID NO 1
<211> LENGTH: 1449
<212> TYPE: DNA
<213> ORGANISM: Lactobacillus curvatus WIKIM55

<400> SEQUENCE: 1
acatgcaagt cgaacgcact ctcgttagat tgaagaagct tgcttctgat tgataacatt      60
tgagtgagtg gcggacgggt gagtaacacg tgggtaacct gccctaaagt ggggggataac    120 atttggaaac agatgctaat accgcataaa acctagcacc gcatggtgca aggttgaaag    180
atggtttcgg ctatcacttt aggatggacc cgcggtgcat tagttagttg gtgaggtaaa    240
ggctcaccaa gaccgtgatg catagccgac ctgagagggt aatcggccac actgggactg    300
agacacggcc cagactccta cgggaggcag cagtagggaa tcttccacaa tggacgaaag    360
tctgatggag caacgccgcg tgagtgaaga aggttttcgg atcgtaaaac tctgttgttg    420
gagaagaacg tatttgatag taactgatca ggtagtgacg gtatccaacc agaaagccac    480
ggctaactac gtgccagcag ccgcggtaat acgtaggtgg caagcgttgt ccggatttat    540
tgggcgtaaa gcgagcgcag gcggtttctt aagtctgatg tgaaagcctt cggctcaacc    600
gaagaagtgc atcggaaact gggaaacttg agtgcagaag aggacagtgg aactccatgt    660
gtagcggtga aatgcgtaga tatatggaag aacaccagtg gcgaaggcgg ctgtctggtc    720
tgtaactgac gctgaggctc gaaagcatgg gtagcaaaca ggattagata ccctggtagt    780
ccatgccgta aacgatgagt gctaggtgtt ggagggtttc cgcccttcag tgccgcagct    840
aacgcattaa gcactccgcc tggggagtac gaccgcaagg ttgaaactca aaggaattga    900
cgggggcccg cacaagcggt ggagcatgtg gtttaattcg aagcaacgcg aagaacctta    960
ccaggtcttg acatcctttg accactctag agatagagct ttccttcgg ggacaaagtg   1020 acaggtggtg catggttgtc gtcagctcgt gtcgtgagat gttgggttaa gtcccgcaac   1080
gagcgcaacc cttattacta gttgccagca tttagttggg cactctagtg agactgccgg   1140
tgacaaaccg gaggaaggtg gggacgacgt caaatcatca tgccccttat gacctgggct   1200
acacacgtgc tacaatggat ggtacaacga gtcgcgagac cgcgaggttt agctaatctc   1260
ttaaaaccat tctcagttcg gattgtaggc tgcaactcgc ctacatgaag ccggaatcgc   1320
tagtaatcgc ggatcagcat gccgcggtga atacgttccc gggccttgta cacaccgccc   1380
gtcacaccat gaagagtttg taacacccaa agccgggtga ggtaaccttc gggagccagc   1440
cgtctaagg                                                          1449
```